United States Patent [19]

Dudeck et al.

[11] 4,229,590

[45] Oct. 21, 1980

[54] PREPARATION OF ALKYL PYRUVATES

[75] Inventors: Christian Dudeck, Limburgerhof; Gunter Lehmann, Ludwigshafen; Bernd Meissner, Heidelberg; Hans Diem, Mannheim; Werner Fliege, Otterstadt; Norbert Petri, Frankenthal; Karl-Heinz Ross, Mutterstadt, all of Fed. Rep. of Germany

[73] Assignee: BASF Aktiengesellschaft, Fed. Rep. of Germany

[21] Appl. No.: 10,725

[22] Filed: Feb. 8, 1979

[30] Foreign Application Priority Data

Mar. 4, 1978 [DE] Fed. Rep. of Germany ....... 2809421

[51] Int. Cl.$^2$ .................... C07C 67/30; C07C 67/42; C07C 69/67
[52] U.S. Cl. .................................. 560/174; 562/577
[58] Field of Search ...................... 560/174; 562/577

[56] References Cited

U.S. PATENT DOCUMENTS

| 1,614,195 | 1/1927 | Haussler | 560/174 |
| 1,627,091 | 5/1927 | Haussler | 562/577 |

FOREIGN PATENT DOCUMENTS

447838  3/1923  Fed. Rep. of Germany ........... 562/577

OTHER PUBLICATIONS

Kulka, Can. J. Res., 24 (1946) pp. 221–223.
Ullmanns Encyklopadie der Technischen Chemie, vol. 4, pp. 726–727.

*Primary Examiner*—Vivian Garner
*Attorney, Agent, or Firm*—Keil & Witherspoon

[57] ABSTRACT

Alkyl pyruvates are prepared by oxidizing alkyl lactates in the presence of a silver catalyst of a defined particle size, at from 450° to 700° C. The products are starting materials for the preparation of drugs, synthetic resins and plastics.

11 Claims, No Drawings

PREPARATION OF ALKYL PYRUVATES

The invention relates to a novel process for the preparation of alkyl pyruvates by oxidizing alkyl lactates in the presence of a silver catalyst of a defined particle size at from 450° to 700° C.

German Pat. No. 447,838 describes a process whereby esters of oxo-acids are prepared from the corresponding esters of hydroxy-acids by reaction in the gas phase with air over a catalyst. The catalyst is an acidic oxide derived from an element which can exist in several oxidation levels, or is a metal salt of an acid derived from such as oxide. The catalyst may also be supported on a carrier, for example copper. The reaction temperature is from 200° to 400° C. Yields of from 60 to 70 percent of theory are described. In the case of the oxidation of alkyl lactates, the Examples only refer to vanadium pentoxide as the catalyst. Silver vanadate is only used for the oxidation of ethyl glycolate. It is a disadvantage that the oxidation, instead of being carried out with air, must be carried out with excess oxygen and that 10 meter long reaction tubes must be used.

Example 4 indicates that the end product still contains a few percent of unconverted lactic acid ester. However, Can. J. Res., 24 (1946), 221 discloses that mixtures of ethyl lactate and ethyl pyruvate are difficult to separate by fractional distillation, so that obtaining the esters in a pure form from this process is only possible with considerable expenditure for equipment.

In order to avoid the difficult separation of the end product from the starting product, it is necessary, according to Can. J. Res. (loc. cit.), pages 221-223, to have a catalyst which effects complete conversion of the ethyl lactate to ethyl pyruvate. A platinum gauze electrolytically coated with platinum black gives, with good conversion, a yield of 68 percent. The catalyst is uneconomical and expensive to regenerate, and has a life of only about 45 hours. The space-time yield is only 0.085 gram per cubic centimeter of catalyst volume per hour. It is pointed out that various metal catalysts, including silver on copper wire gauze, are insufficiently active; at 250°-300° C. they give a conversion of 35-50 percent.

In the light of the prior art, Ullmanns Encyklopädie der Technischen Chemie, volume 4, page 727 points out that in spite of various possible methods of synthesis, heating tartaric acid with potassium bisulfate remains the best method of preparation of pyruvic acid. This process is stated to give a yield of 50-55 percent of theory.

All these processes are unsatisfactory in respect of simplicity and economy of operation, yield and space-time yield, and in respect of simplicity of working-up and of purity of the end product.

We have found that an alkyl pyruvate of the formula

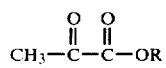
I where R is an aliphatic radical, is obtained in an advantageous manner by oxidizing a lactic acid ester in the presence of a metal catalyst at an elevated temperature, if an alkyl lactate of the formula

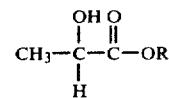
II where R has the above meaning, is oxidized in the presence of silver crystals, having a particle size of from 0.01 micrometer to 2.5 millimeters, as the catalyst, at from 450° to 700° C.

Further, it has been found that the process may be carried out advantageously if the catalyst contains a proportion of silver crystals having a particle size of from 0.01 to 10 micrometers and a proportion of silver crystals having a particle size of from 0.2 to 2.5 millimeters.

Where ethyl lactate is used, the reaction can be represented by the following equation:

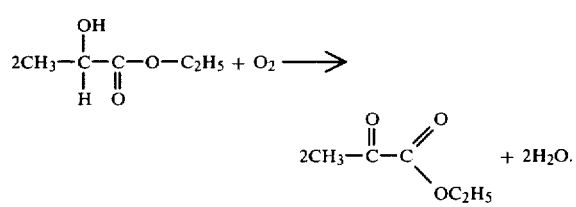

Compared to the prior art, the process according to the invention surprisingly gives, more simply and more economically, a better overall result in respect of yield, space-time yield, purity of the end product and life of the catalyst. The life of the catalyst is as a rule at least 123 days in the case of ethyl pyruvate. All these advantageous results are surprising in view of the prior art, especially in view of the teaching in Can. J. Res. (loc. cit.), since, bearing in mind the high temperatures used according to the invention, and the catalyst according to the invention, at least a substantial decrease in yield and substantial formation of decomposition products would have been expected. In general, using the esters of lower alkanols, especially at from 540° to 600° C., with throughputs of from 0.8 to 1 t/m$^2$·h and conversions of 96-99 percent, yields of 65-75% of theory and space-time yields of 10-24 g/cm$^3$·h are obtained. The n-alkyl pyruvate can, if desired, be hydrolyzed to give pyruvic acid.

If the presence of small amounts of starting material does not interfere, for example if the end product is used directly, without purification, for the preparation of pyruvic acid, the reaction can, for example, be carried out at from 540° to 600° C. with a throughput of 1.1-1.5 t/m$^2$·h, thereby achieving, at 85-90 percent conversion, a yield of 80-85 percent of theory and a space-time yield of 25-50 g/cm$^3$·h. Expensive processing of the catalyst, and expensive reactors, are avoided.

The catalyst can be regenerated comparatively easily. Silver crystals of all particle sizes, such as are obtained by electrolytic production of granular silver, are used. Accordingly, electrolysis installations are better utilized in the case of the process according to the invention, and their size can be selected accordingly; energy, labor and auxiliary materials, for example nitric acid, are saved, and such operations as washing, screening and drying of the silver are simplified.

Preferred starting materials II and, accordingly, preferred end products I are those where R is alkyl of 1 to 7 carbon atoms. The said radical can be substituted by groups which are inert under the reaction conditions, for example alkyl of 1 to 4 carbon atoms.

Examples of suitable starting materials II are methyl, ethyl, n-propyl, isopropyl, n-butyl, sec.-butyl, isobutyl, tert.-butyl, pentyl, hexyl and heptyl lactate.

The oxidizing agent used may be either pure oxygen or a gas containing free oxygen, in particular air. Oxygen, as a rule in the form of air, and the starting material II are advantageously employed in a molar ratio of from 0.25 to 0.9, especially from 0.35 to 0.7, mole of oxygen per mole of starting material II. The use of an inert gas is not necessary but on the other hand does not interfere with the reaction. If desired, the catalyst can be heated by means of hot inert gases, advantageously nitrogen or low-soot combustion gases which do not contain any catalyst poison and are, for example, at from 600° to 800° C.

Suitable starting materials for the process are pure alkyl lactates, or technical-grade alkyl lactates, i.e. products which are separated off directly after their process of preparation and have not been subjected to a purification operation, or mixtures of these esters with water; the concentration of the ester in the aqueous mixtures can advantageously be from 60 to 95 percent by weight, preferably from 70 to 90 percent by weight. Advantageously, the reaction is carried out with a ratio of from 0.67 to 0.05, preferably from 0.43 to 0.11, gram of water per gram of starting material II. The alkyl lactate is fed, to the reaction chamber, in the form of vapor, which may or may not be mixed with steam and/or inert gas.

The total thickness of the catalyst bed is advantageously from 10 to 50, preferably from 20 to 30, millimeters. All particle sizes from 0.01 micrometer to 2.5 millimeters, preferably from 0.1 millimeter to 2.5 millimeters, can be used in the catalyst, and it is advantageous to mix homogeneously all the particle sizes in the catalyst bed. It is true, however, that the catalyst can also be built up from all the above particle sizes, but with these arranged in 2, 3 or more layers according to particle size. If all particle sizes are used in the catalyst, a 2-layer catalyst and in particular a single-layer catalyst are preferred. In the case of multi-layer catalysts, for example in the 2-layer or 3-layer catalyst of a usually vertical reactor, the catalyst particles in the form of silver crystals are arranged, according to particle size, in an upper and lower part of the total bed (2-layer catalyst) or in an upper, middle and lower part of the total bed (3-layer catalyst). The starting mixture consisting of the vapor of the starting material II and oxygen or air, with or without steam and inert gas, is in general passed downward, so that the upper layer or upper layers constitute the part facing the starting mixture. If reactors of different construction are used, or if the starting mixture is passed through the reactor differently, all statements in the description relating to the upper (lower) part of the catalyst apply similarly to the corresponding part facing the starting mixture (the issuing reaction mixture), for example, in the case of a horizontal reactor, to the front (rear) part of the catalyst.

Where all particle sizes are used in a 2-layer catalyst, the upper silver layer preferably accounts for from 5 to 30, preferably from 10 to 20, percent by weight and contains particles having a size of from 0.01 micrometer to 0.75 millimeter, whilst the lower silver layer accounts for from 70 to 95, preferably 80 to 90, percent by weight and contains particles having a size of from 0.75 to 2.5 millimeters. In a preferred embodiment, not all particle sizes are used, but only the coarse fraction of silver crystals, having a particle size of from 0.1 to 2.5 millimeters. Catalysts in which all the silver layers only contain these coarser silver crystals are hereafter referred to as coarse catalysts.

The coarse proportion of the crystals (particle size from 0.1 to 2.5 millimeters) can be located in one layer or in several layers, preferably in one, 2 or 3 layers. In a single-layer catalyst, the coarse fraction is preferably present homogeneously distributed throughout the entire catalyst. In a 2-layer catalyst, the upper silver layer preferably accounts for from 5 to 30, preferably from 10 to 20, percent by weight and contains particles having a size of from 0.1 to 0.75 millimeter, whilst the lower silver layer accounts for from 70 to 95, preferably from 80 to 90, percent by weight, and contains particles having a size of from 0.75 to 2.5 millimeters.

If the coarse constituent is arranged in 3 layers, then advantageously the lower part contains from 72.5 to 89, preferably from 77.5 to 82.5, percent by weight of all catalyst particles, the middle part contains from 2.5 to 7.5, preferably from 4.5 to 6.5, percent by weight of all catalyst particles and the upper part contains from 8.5 to 20, preferably from 13 to 16, percent by weight of all catalyst particles. The particles of the lower layer advantageously have a size of from 1 to 2.5 millimeters, those of the middle layer from 0.75 to 1 millimeter and those of the upper layer, from 0.1 to 0.75 millimeter. Each layer (coarse constituent) can itself consist of one or more sub-layers, preferably of 1 to 2 sub-layers. A coarse catalyst comprising 2 to 4 layers is preferred. Each of these layers differs from the other in the particle size of the silver crystals and in most cases also in respect of the proportion by weight of the total coarse catalyst.

If the upper layer possesses 2 sub-layers, the lower of these preferably accounts for from 0.5 to 2 percent by weight of the total catalyst and contains particles having a size of from 0.1 to 0.4 millimeter, and the upper part accounts for from 8 to 18 percent by weight and contains particles having a size of from 0.4 to 0.75 millimeter. Accordingly, the following are preferred, in respect of proportion by weight and particle size, in the case of the middle layer:

2 sub-layers:
 upper sub-layer 1.5–4.5% by weight (0.75–0.9 mm)
 lower sub-layer 1–3% by weight (0.9–1 mm).

In the case of the lower layer, the following are preferred:

2 sub-layers:
 upper sub-layer 7.5–22.5% by weight (1–1.75 mm)
 lower sub-layer 50–81.5% by weight (1–2.5 mm).

The finely granular silver (particle size of from 0.01 to 10 μm) can be prepared by conventional methods, for example in the course of the production of silver, by employing appropriate milling operations and screening operations, or by preparing it in the form of Raney silver. Regarding the methods of preparation of silver, reference may be made to Ullmanns Encyklopädie der technischen Chemie, volume 15, pages 636–666. Silver can also be precipitated from appropriate solutions, for example silver nitrate solutions, by precipitants such as hydrazine or formaldehyde, and can also be obtained by electrolysis.

Advantageously, the throughput employed in the reaction is from 0.5 to 3 t, especially from 0.8 to 1.8 t, of starting material II per $m^2$ of catalyst bed cross-section per hour. In industrial operation, the catalyst bed diameter is preferably at least 0.1 meter, advantageously from 0.2 to 3 meters.

To carry out the oxidation, the gas mixture consisting of the vapor of starting material II and of air, with or without inert gas and with or without steam is passed, in the above amounts, through the silver catalyst at from about 450° to 700° C., especially from 540° to 600° C. The process is in general carried out continuously, under a pressure of from 0.5 to 2 bar, preferably from 0.8 to 1.8 bar. It is advantageous to cool the reaction gases, leaving the catalyst zone, within a short time, for example to 20° C. The cooled gas mixture is then advantageously fed to an absorption tower in which the end product is washed out of the gas mixture with water, advantageously in counter-current.

The alkyl pyruvates obtainable by the process of the invention are valuable starting materials for the preparation of drugs, synthetic resins and plastics. They can be hydrolyzed to give pyruvic acid, for example by means of water at 80°–100° C. in the presence of a cation exchanger.

Regarding uses, reference may be made to Ullmann, loc. cit., page 727.

In the examples which follow, parts are by weight.

EXAMPLE 1

An installation comprising a vaporizer and a vertical tubular reactor is employed. The top of the reactor comprises the feed for the starting mixture, which is in vapor form, and the reactor cover. The catalyst layer is below the reactor head, followed, lower still, by a cooling zone. The reactor is connected to an absorption column.

A catalyst comprising 187 parts of silver crystals and made up as shown below is introduced into the reactor:

|         | Proportion in the catalyst (% by weight) | Particle size (mm) |
|---------|------------------------------------------|--------------------|
| Layer 1 | 14.1                                     | 0.1–0.75           |
| Layer 2 | 5.9                                      | 0.75–1             |
| Layer 3 | 80.0                                     | 1–2.5              |

Per hour, a mixture of 2,051 parts of ethyl lactate and 1,220 parts of air is fed to the vaporizer and the ester is vaporized. The starting mixture, in vapor form, is passed through the catalyst and reacted at 550° C. and 1.4 bar. The throughput is 0.9 t/m². The gaseous reaction mixture is cooled to 20° C. and then washed with water. 1,371 parts per hour of ethyl pyruvate of boiling point 155° C., corresponding to a yield of 68% of theory, and 41 parts per hour of unconverted starting material II are obtained, the product being in the form of a 72 percent stregnth by weight solution. The space-time yield is 20 g/cm³·h. The life of the catalyst is 123 days and the conversion is 98 percent.

EXAMPLE 2

The same installation as in Example 1 is used. A catalyst comprising 187 parts of silver crystals and made up as shown below is introduced into the reactor:

|         | Proportion in the catalyst (% by weight) | Particle size (mm) |
|---------|------------------------------------------|--------------------|
| Layer 1 | 18.5                                     | 0.1–0.75           |
| Layer 2 | 81.5                                     | 0.75–2.5           |

Per hour, a mixture of 2,880 parts of ethyl lactate and 2,250 parts of air is fed to the vaporizer and vaporized. The starting mixture, in vapor form, is passed through the catalyst and reacted at 550° C. and 1.4 bar. The throughput is 1.27 t/m²·h. The gaseous reaction mixture is cooled to 20° C. and washed with water. 2,322 parts per hour of ethyl pyruvate of boiling point 155° C., corresponding to a yield of 82% of theory, and 31.7 parts per hour of unconverted starting material II are obtained, the product being in the form of an 84 percent strength by weight solution. The space-time yield is 35 g/cm³·h. The life of the catalyst is 130 days and the conversion is 89 percent.

EXAMPLE 3

The reaction is carried out as described in Example 2, with the same catalyst, but with a particle size of from 0.01 micrometer to 0.75 millimeter in the upper layer of silver. The same results are obtained.

EXAMPLE 4

The reaction is carried out as described in Example 1, but with methyl lactate. The throughput is 0.9 t/m²·h. 1,448 Parts per hour of methyl pyruvate, of boiling point 135° C., corresponding to a yield of 72% of theory, and 20.5 parts per hour of unconverted starting material II are obtained. The life of the catalyst is 123 days and the conversion is 99 percent. The space-time yield is 21 g/cm³·h.

We claim:

1. A process for the preparation of an alkyl pyruvate of the formula

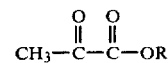

where R is an alkyl radical, by oxidizing a lactic acid ester in the presence of a metal catalyst at an elevated temperature, wherein an alkyl lactate of the formula

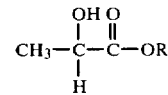

where R has the above meaning, is reacted with free oxygen in the presence of a catalyst of silver crystals having a particle size of from 0.01 micrometer to 2.5 millimeters, at from 450° to 700° C.

2. The process of claim 1, wherein the reaction is carried out with a catalyst which comprises a proportion of silver crystals having a particle size of from 0.01 to 10 micrometers and a proportion of silver crystals having a particle size of from 0.2 to 2.5 millimeters.

3. The process of claim 1, wherein the reaction is carried out with a molar ratio of from 0.25 to 0.9 mole of oxygen, in the form of air, per mole of starting material II.

4. The process of claim 1, wherein the reaction is carried out with a ratio of from 0.67 to 0.05 gram of water per gram of starting material II.

5. The process of claim 1, wherein the reaction is carried out with a total thickness of the catalyst bed of from 10 to 50 millimeters.

6. The process of claim 1, wherein the reaction is carried out in a 2-layer catalyst, comprising an uper silver layer which accounts for from 5 to 30 percent by weight and contains silver particles having a size of from 0.01 micrometer to 0.75 millimeter, and a lower silver layer which accounts for from 70 to 95 percent by weight and contains silver particles having a size of from 0.75 to 2.5 millimeters.

7. The process of claim 1, wherein the reaction is carried out with a catalyst comprising only silver crystals having a particle size of from 0.1 to 2.5 millimeters.

8. The process of claim 1, wherein the reaction is carried out in a 2-layer catalyst, comprising an upper silver layer which accounts for from 5 to 30 percent by weight and contains silver particles having a size of from 0.1 to 0.75 millimeter, and a lower silver layer which accounts for from 70 to 95 percent by weight and contains particles of silver crystals having a size of from 0.75 to 2.5 millimeters.

9. The process of claim 1, wherein the reaction is carried out in a three layer catalyst bed which comprises, in the lower part, from 72.5 to 89 percent by weight of all silver catalyst particles, in the middle part, from 2.5 to 7.5 percent by weight of all silver catalyst particles and in the upper part, from 8.5 to 20 percent by weight of all silver catalyst particles, the particle sizes being from 1 to 2.5 millimeters in the lower part, from 0.75 to 1 millimeter in the middle part and from 0.1 to 0.75 millimeter in the upper part.

10. The process of claim 1, wherein the reaction is carried out at from 540° to 600° C.

11. The process of claim 1, wherein the reaction is carried out at a pressure of from 0.5 to 2 bar.

* * * * *